United States Patent
Marino (10) Patent No.: US 7,951,152 B2
(45) Date of Patent: May 31, 2011

(54) SPINAL DISTRACTOR, COMPRESSOR, AND ROD ENGAGING SYSTEM AND METHOD

(75) Inventor: James F. Marino, La Jolla, CA (US)

(73) Assignee: Trinity Orthopedics, LLC, San Diego, CA (US)

( * ) Notice: Subject to any disclaimer, the term of this patent is extended or adjusted under 35 U.S.C. 154(b) by 453 days.

(21) Appl. No.: 11/604,134

(22) Filed: Nov. 24, 2006

(65) Prior Publication Data

US 2009/0036895 A1 Feb. 5, 2009

(51) Int. Cl.
*A61B 17/70* (2006.01)

(52) U.S. Cl. ........... 606/86 A; 606/57; 606/58; 606/279

(58) Field of Classification Search ............ 606/57, 606/58, 60, 86 A, 86 R, 90, 102, 104, 105, 606/279
See application file for complete search history.

(56) References Cited

U.S. PATENT DOCUMENTS

| | | | | |
|---|---|---|---|---|
| 5,700,263 | A * | 12/1997 | Schendel | 606/57 |
| 6,146,386 | A * | 11/2000 | Blackman et al. | 606/103 |
| 6,290,724 | B1 | 9/2001 | Marino | |
| 6,565,568 | B1 | 5/2003 | Rogozinski | |
| 6,716,218 | B2 | 4/2004 | Holmes et al. | |
| 6,886,662 | B2 * | 5/2005 | Riley | 182/82 |
| 7,588,575 | B2 * | 9/2009 | Colleran et al. | 606/86 A |
| 2003/0060826 | A1 * | 3/2003 | Foley et al. | 606/61 |
| 2003/0229347 | A1 * | 12/2003 | Sherman et al. | 606/61 |
| 2005/0038432 | A1 | 2/2005 | Shaolian et al. | |
| 2005/0277934 | A1 * | 12/2005 | Vardiman | 606/61 |

* cited by examiner

*Primary Examiner* — Eduardo C Robert
*Assistant Examiner* — Steven J Cotroneo
(74) *Attorney, Agent, or Firm* — Fred C. Hernandez; Mintz, Levin, Cohn, Ferris, Glovsky, and Popeo P.C.

(57) ABSTRACT

Apparatus and methods for distracting or compressing distance between a first and second boney structure and for engaging a connecting element.

14 Claims, 11 Drawing Sheets

SPINAL DISTRACTOR, COMPRESSOR, AND ROD ENGAGING SYSTEM AND METHOD

BACKGROUND

1. Field of the Invention

The invention relates generally to apparatus and methods for distracting or compressing the distance between a first and second boney structure.

2. Description of Related Art

It is desirable to enable a user to distract or compress the distance between a first and second boney structure. The present invention provides such a system and method.

SUMMARY OF THE INVENTION

The present invention includes apparatus and methods for controllably distracting or compressing the distance between a first and second boney structure via a connecting element.

BRIEF DESCRIPTION OF THE DRAWINGS

The features, objects, and advantages of the present invention will become more apparent from the detailed description set forth below when taken in conjunction with the drawings in which like reference characters identify correspondingly throughout and wherein.

DETAILED DESCRIPTION

Throughout this description, embodiments and variations are described for the purpose of illustrating uses and implementations of the invention. The illustrative description should be understood as presenting examples of the invention, rather than as limiting the scope of the invention.

Figure 1A:
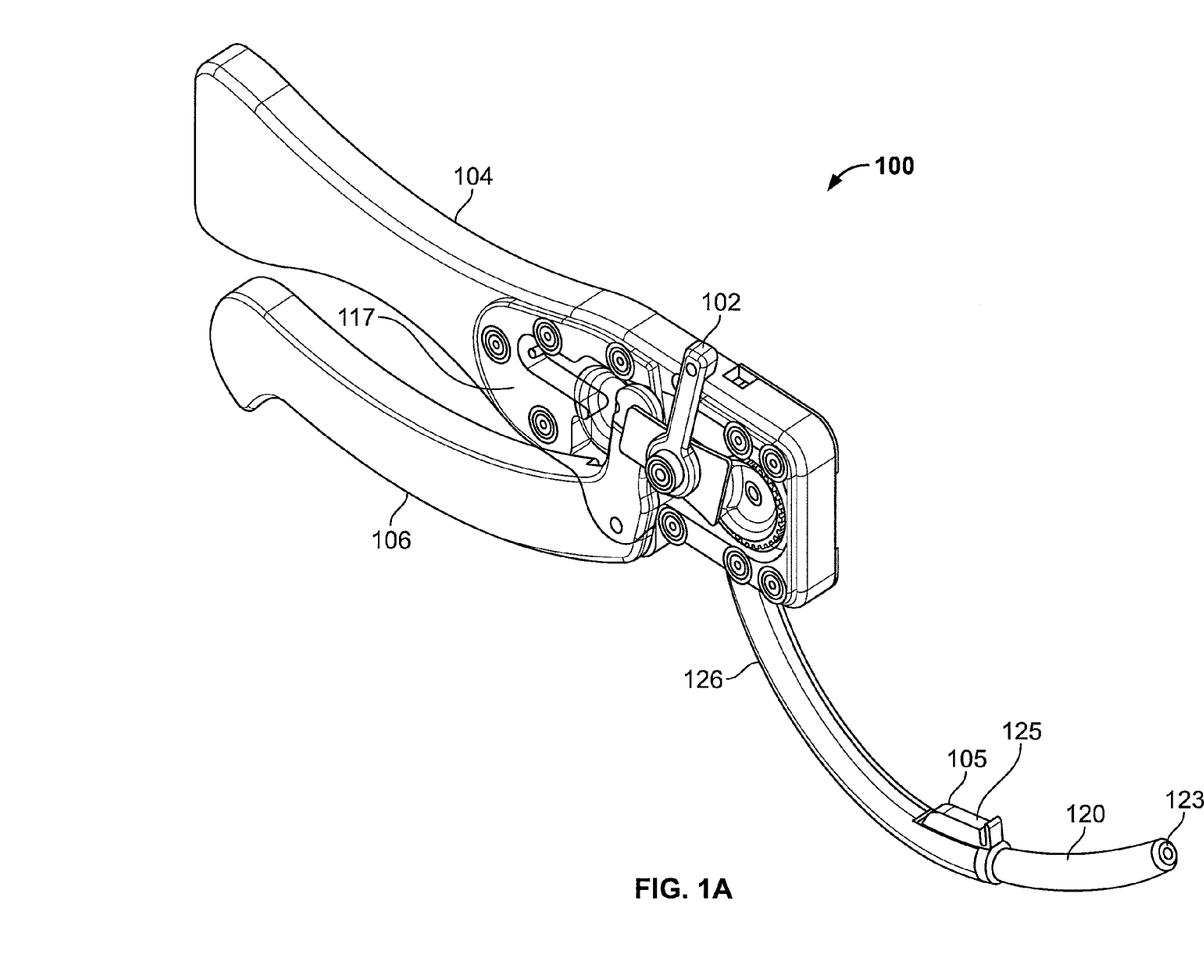
FIG. 1A is an isometric diagram of a compressor and distracter apparatus coupled to a connecting element according to various embodiments.

FIG. 1A is an isometric diagram of a compressor and distracter apparatus 100 coupled to a connecting element 120 according to various embodiments. The apparatus 100 includes a ratchet body or base 104, ratchet mechanism 117, ratchet actuator handle 106, ratchet direction selector 102, slidable hook 105, and hook slide recess and connecting element holder 126. The hook slide 105 is coupled to the ratchet mechanism 117 where the slide 105 moves relative to the connecting element holder 126. The slide 105 may move toward or away from the connecting element 126 as a function of the ratchet direction selection 102. In operation, the connecting element 120 distal end 123 may be fixably coupled to a first bony structure (12 in FIG. 2A). The hook slide catch 125 may be physically coupled to a second bony structure (14 in FIG. 2A). As the ratchet mechanism 117 is operated by handle 106 the second bony structure 14 may be compressed toward or distracted away the first bony structure 12. Due the ratchet mechanism 117, the compression or distraction is controllably performed in discrete increments based on the direction 102 and handle actuations 106.

Figure 1B:
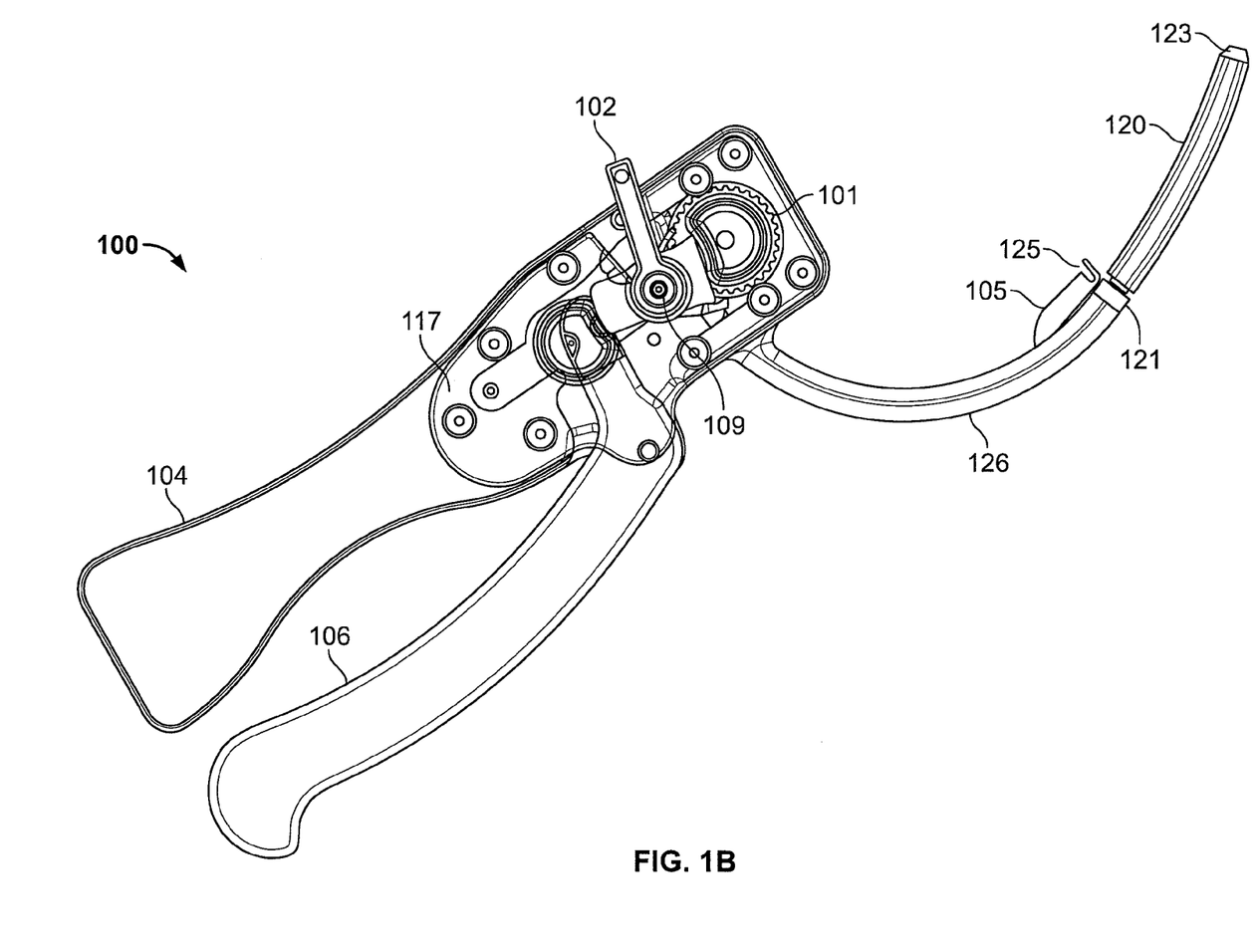
FIG. 1B is a side, partial sectional diagram of a compressor and distracter apparatus coupled to a connecting element according to various embodiments.

The connecting element holder 126 may have a curvature radius, R1. The connecting element 120 may a curvature radius, R2. In embodiment R1 may be similar to R2 to enable smooth compression or distraction between two bony structures 12, 14. Further, movement between the bony structures 12, 14 may follow a curvature radius, R3 where R1 and R2 are similar to R3. In spinal applications R3 may be approximately equal to the lordosis between a first vertebra 12 and a second vertebra 14. FIG. 1B is a side, partial sectional diagram of the compressor and distracter apparatus 100 coupled to a connecting element 120 according to various embodiments. The apparatus 100 includes a master pin 109 and main ratchet gear 101. The master pin 109 is couples the direction selector 102 to the ratchet mechanism 117. The main ratchet gear 101 have a fixed number of gears having a fixed tooth shape and size. The gear 101 is coupled to reciprocal teeth in the hook slide (124 in FIGS. 1D and 1E). Accordingly, when the ratchet mechanism 117 is actuated (via handle 106), the hook slide 105 is moved a fixed, predetermined distance, permitting an apparatus 100 user to controllably distract or compress the space or distance between two bony structures 12, 14.

Figure 1C:
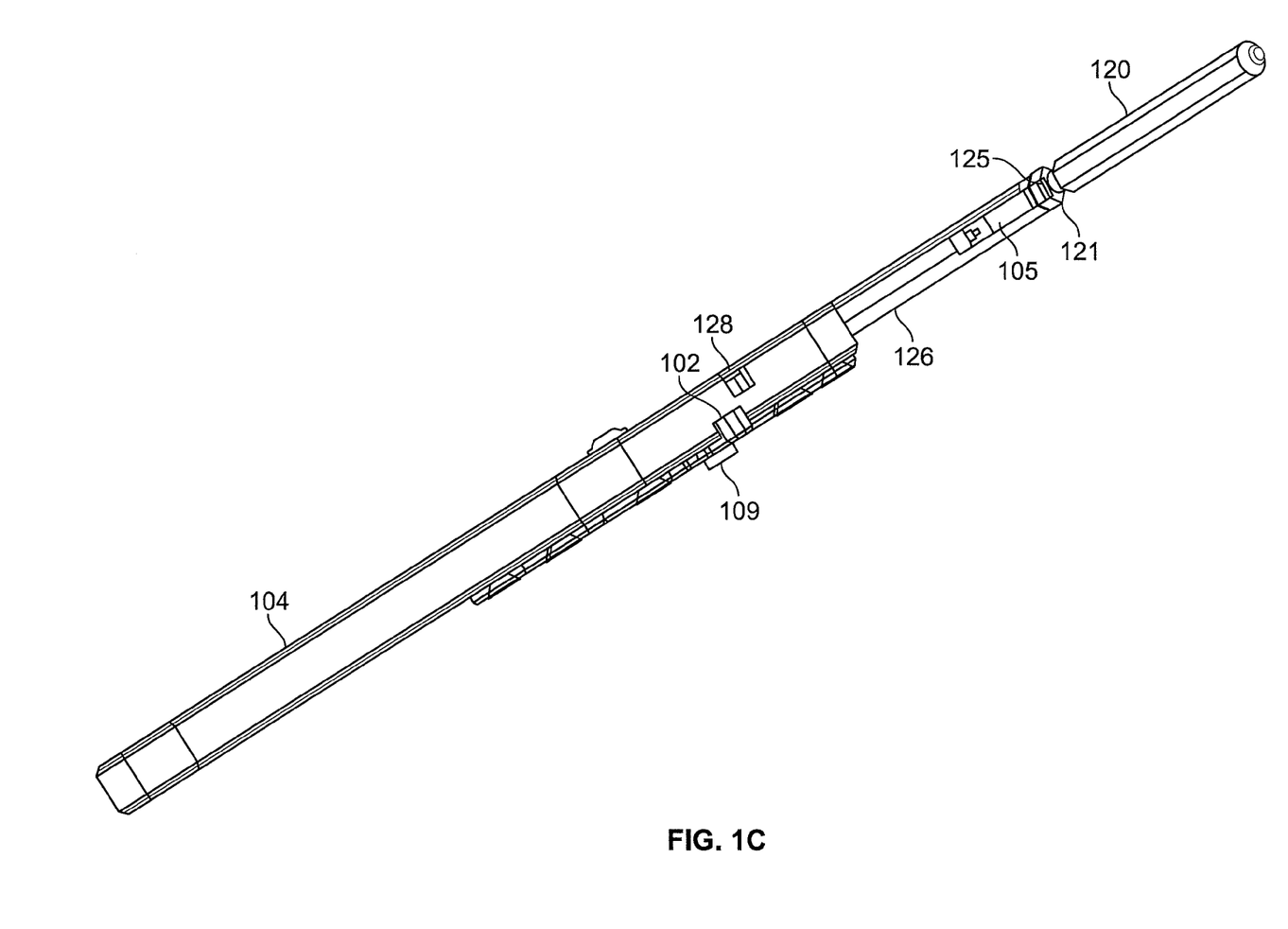
FIG. 1C is a top diagram of a compressor and distracter apparatus coupled to a connecting element according to various embodiments.

FIG. 1C is a top diagram of a compressor and distracter apparatus 100 coupled to a connecting element 120 according to various embodiments. The apparatus 100 may include a connecting element connector 121. The connecting element connector 121 may include a compressible collet that may be inserted into a connecting element 120 recess (122 in FIG. 1E). In an embodiment after the collet 121 is inserted into the connecting element 120 recess 122, a locking pin (109 in FIG. 1E) may be inserted into the collet 121 via the locking pin 109 actuator 128 (FIG. 1C). The locking pin 109 insertion may fixably expand the collet 121 within the connecting element 120 recess 122 and prevent separation of the connecting element 120 from the holder 126. In an embodiment the connecting element 120 is a cylindrical rod that is substantially incompressible along its longitudinal axis. The connecting element 120 may be any element 120 may span between two bony structures and a substantially incompressible longitudinal axis. The connecting element 120 may include a dynamic connector where the dynamic connector may be made substantially incompressible along its longitudinal axis during insertion or implantation.

Figure 1D:
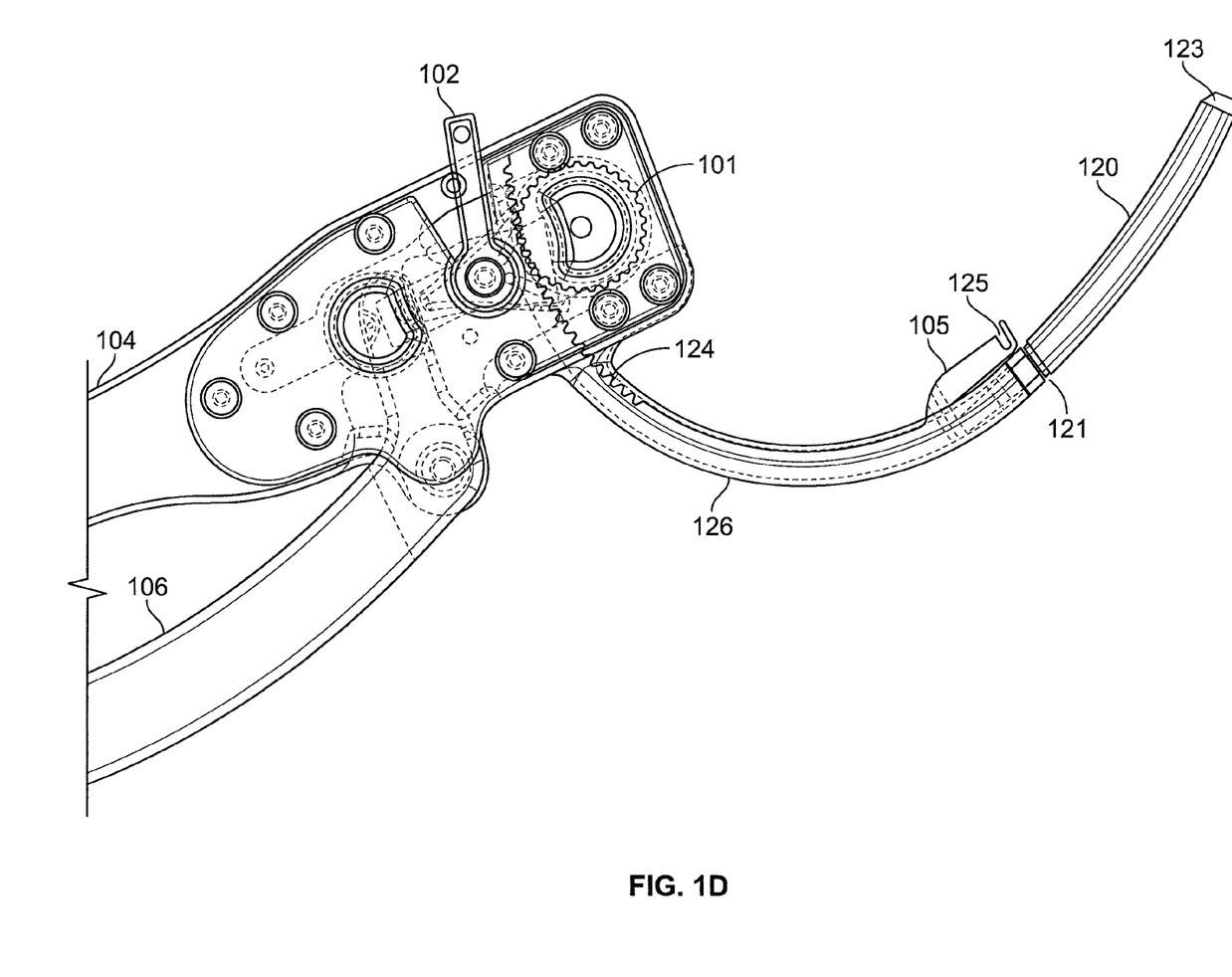
FIG. 1D is a side, sectional diagram of a compressor and distracter apparatus coupled to a connecting element according to various embodiments.

FIG. 1D is a side, sectional diagram of the compressor and distracter apparatus 100 coupled to a connecting element 120 according to various embodiments. As shown in FIG. 1D the connecting element holder 126 includes a sleeve for the hook slide 105. The hook slide 105 includes a plurality of teeth 124 at is proximal end. The teeth 124 are configured to mate with the ratchet mechanism 117 main ratchet gears 101. When the ratchet mechanism 117 is actuated via the handle 106 the hook slide 105 is translated with the connecting element holder 126 so the hook slide 105 catch 125 is moved relative to the fixed connecting element coupler (collet in an embodiment) 121. In an embodiment a first bony structure is fixably coupled to connecting element 120 distal end 123. A second bony structure may be fixably coupled to another apparatus that is releasably couplable to the hook slide 105 catch 125. The apparatus 100 may then be actuated to translate the hook slide 105 relative to the coupled connecting element 120. Accordingly the second bony structure 14 may be compressed toward or distracted away from the first bony structure 12. In an embodiment the first and the second bony structure may be single anatomical bony structure that has been separated such as long bone fracture.

Figure 1E:
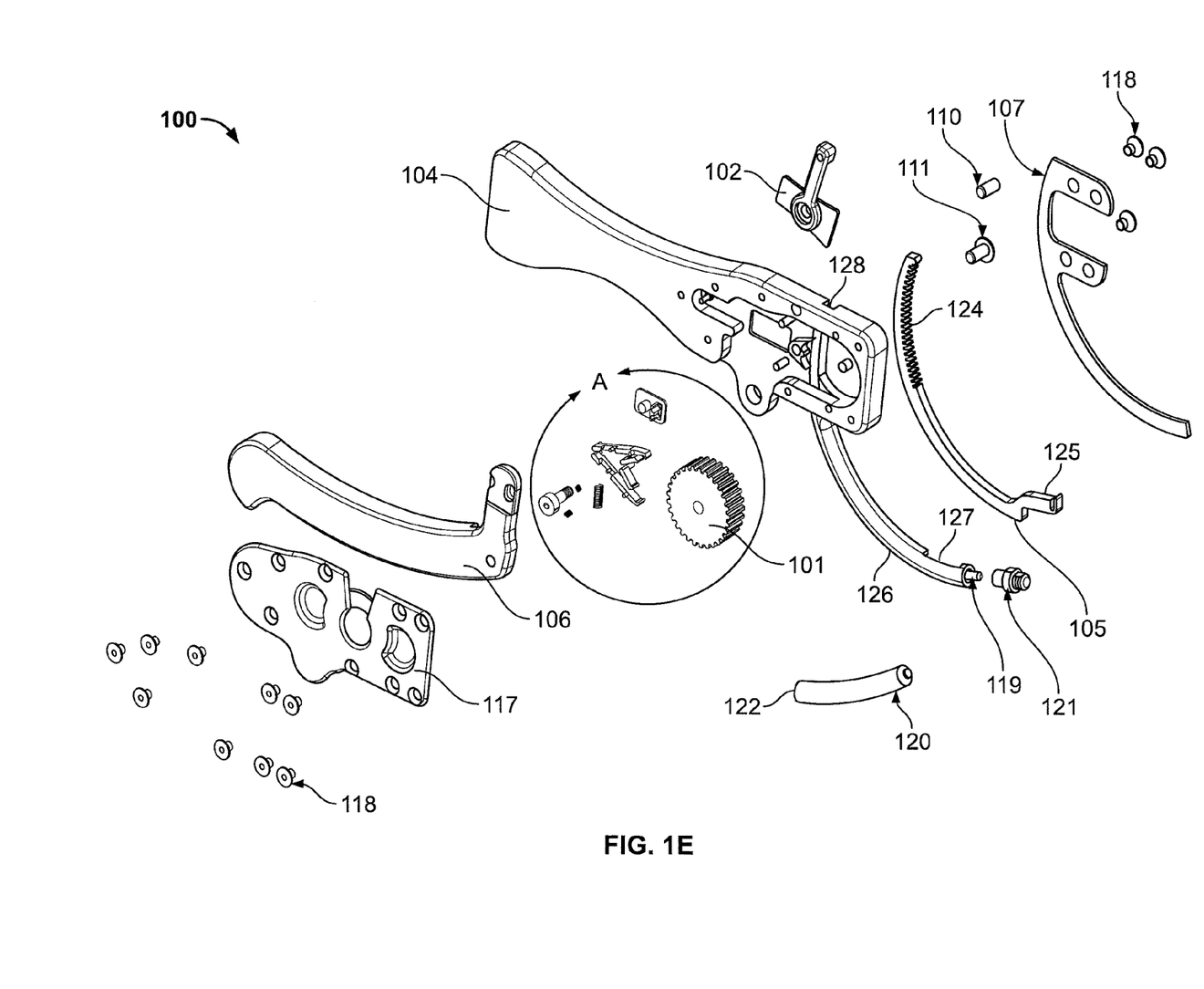
FIG. 1E is an exploded diagram of a compressor and distracter apparatus and a connecting element according to various embodiments.
Figure 1F:
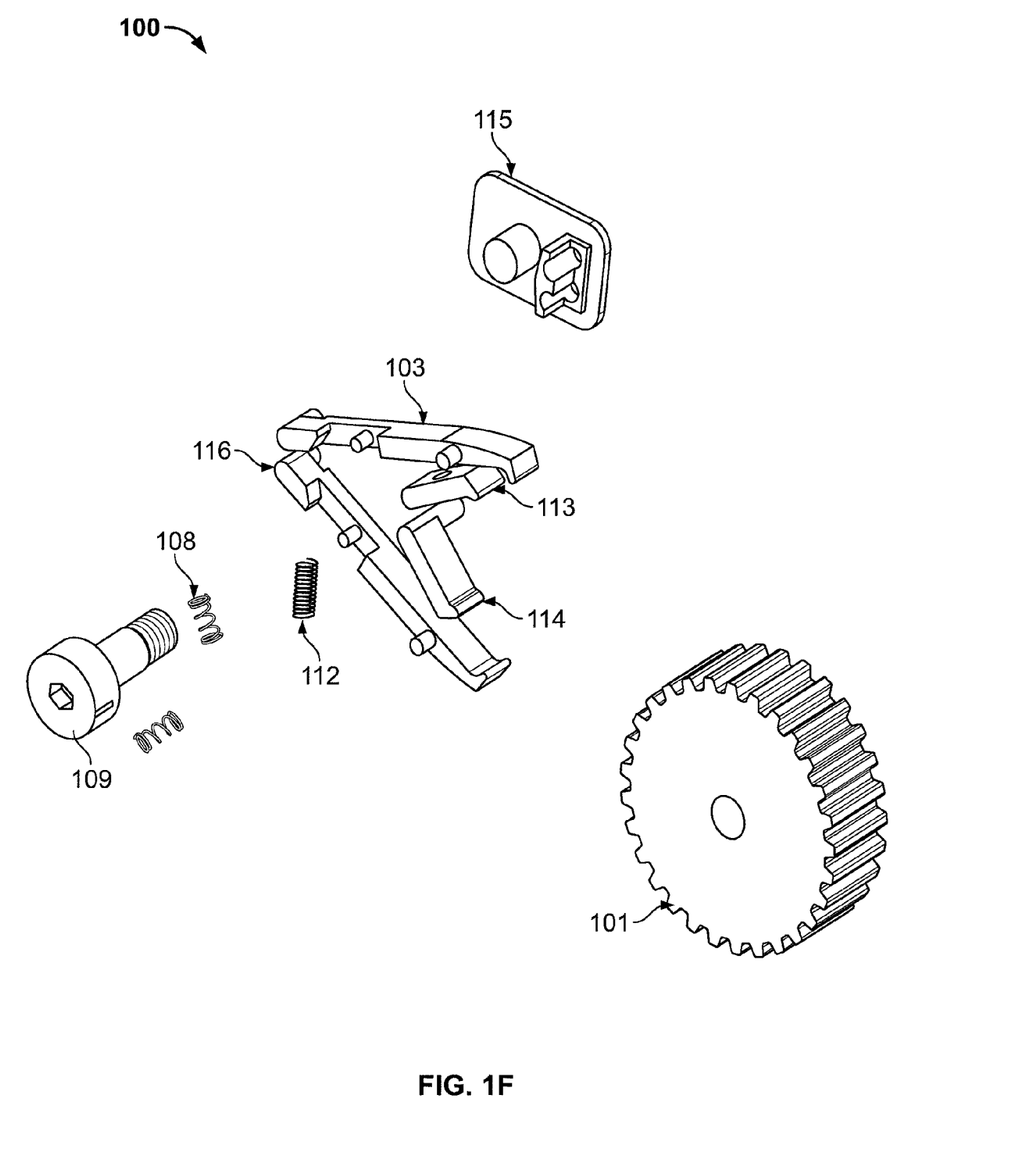
FIG. 1F is an exploded diagram of a section of a compressor and distracter apparatus according to various embodiments.

FIG. 1E is an exploded diagram of the compressor and distracter apparatus 100 and a connecting element 120 according to various embodiments. FIG. 1F is an exploded diagram of a section of the ratchet mechanism 117 of the compressor and distracter apparatus 100 according to various embodiments. The apparatus 100 may include a ratchet housing/handle 104, director selector 102, main ratchet gear 101, pin advancer 103, hook slide 105, ratchet actuator 106, hook slide cover 107, lee spring 108, master pin 109, ball spring plunger 110, screw 111, lee spring 112, ratchet lock pin 113, ratchet lock pin 114, block pin advancer 115, pin advancer 116, ratchet mechanism 117, screws 118, connecting element locking pin 119, connecting element coupler (collet) 121, hook slide gear 124, hook slide recess/connecting element holder 126, slide path 127, and locking pin control 128. As can be shown in FIGS. 1E and 1F the apparatus 100 enables a user to incrementally translate the hook slide 105 relative to the hook slide recess/connecting element holder 126.

Figure 2A:
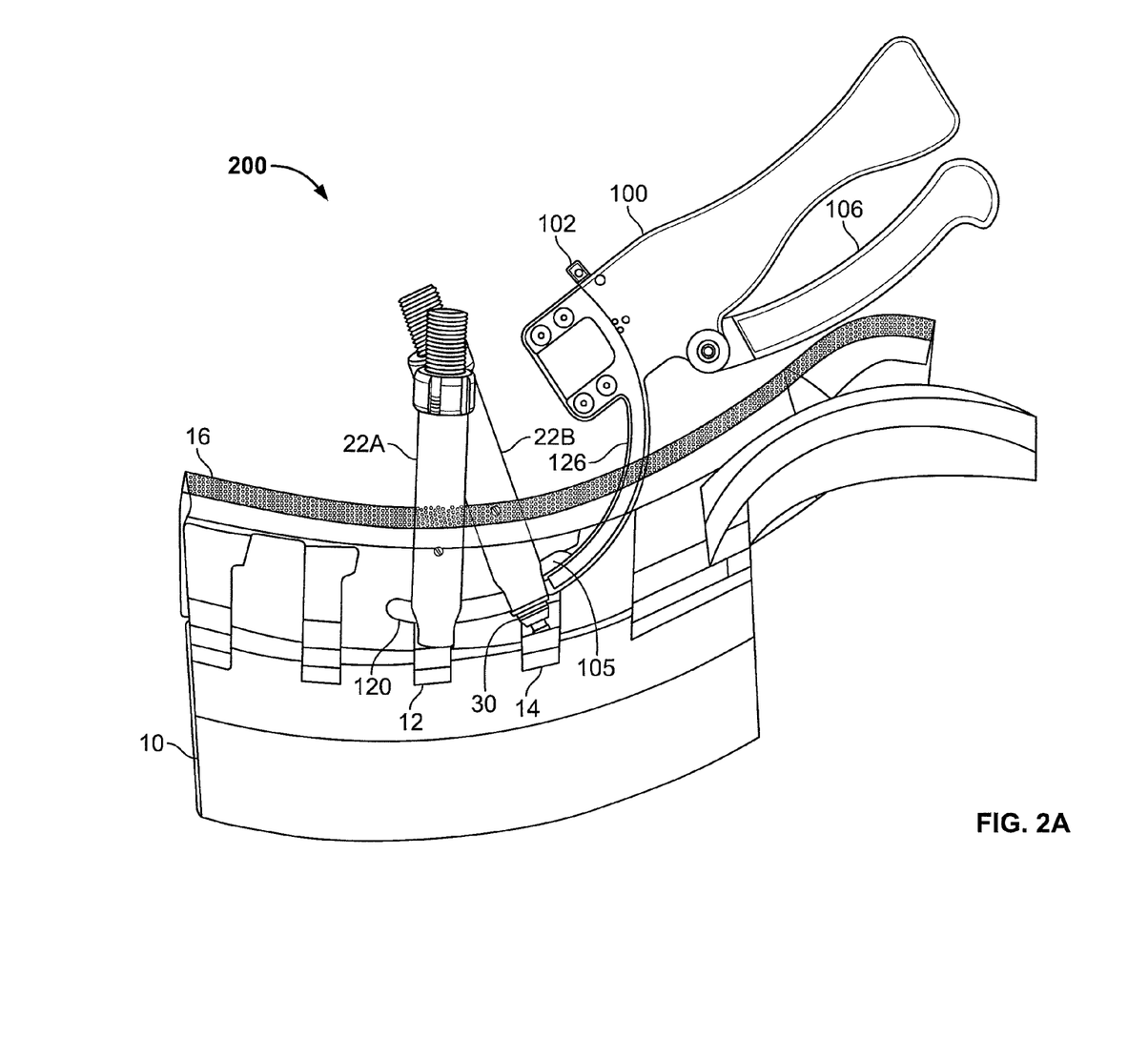
FIG. 2A is a diagram of a compressor and distracter apparatus coupled to a connecting element employed to compress or distract the disc space between two vertebra according to various embodiments.

FIG. 2A is a diagram of a compressor and distracter apparatus 100 coupled to a connecting element 120 employed to compress or distract the disc space 13 between two vertebra 12, 14 of a spine 10 according to various embodiments. The spine 10 may include a plurality of vertebra 12, 14 covered by skin 16. The connecting element 120 may be fixably coupled to the first vertebra 12 via a bone connecting element (30 in FIG. 2B). The hook slide 105 may be coupled to the second vertebra 14 via a bone connecting element 30 and connecting cannula 22B. A connecting cannula 22A may be coupled to first vertebra 12 via the bone connecting element. Depending on the direction selection 102, actuation of handle 106 may distract the second vertebra 14 away from the first vertebra 12 (FIG. 2C) or may compress the second vertebra 14 toward the first vertebra 12 (FIG. 2D).

Figure 2B:
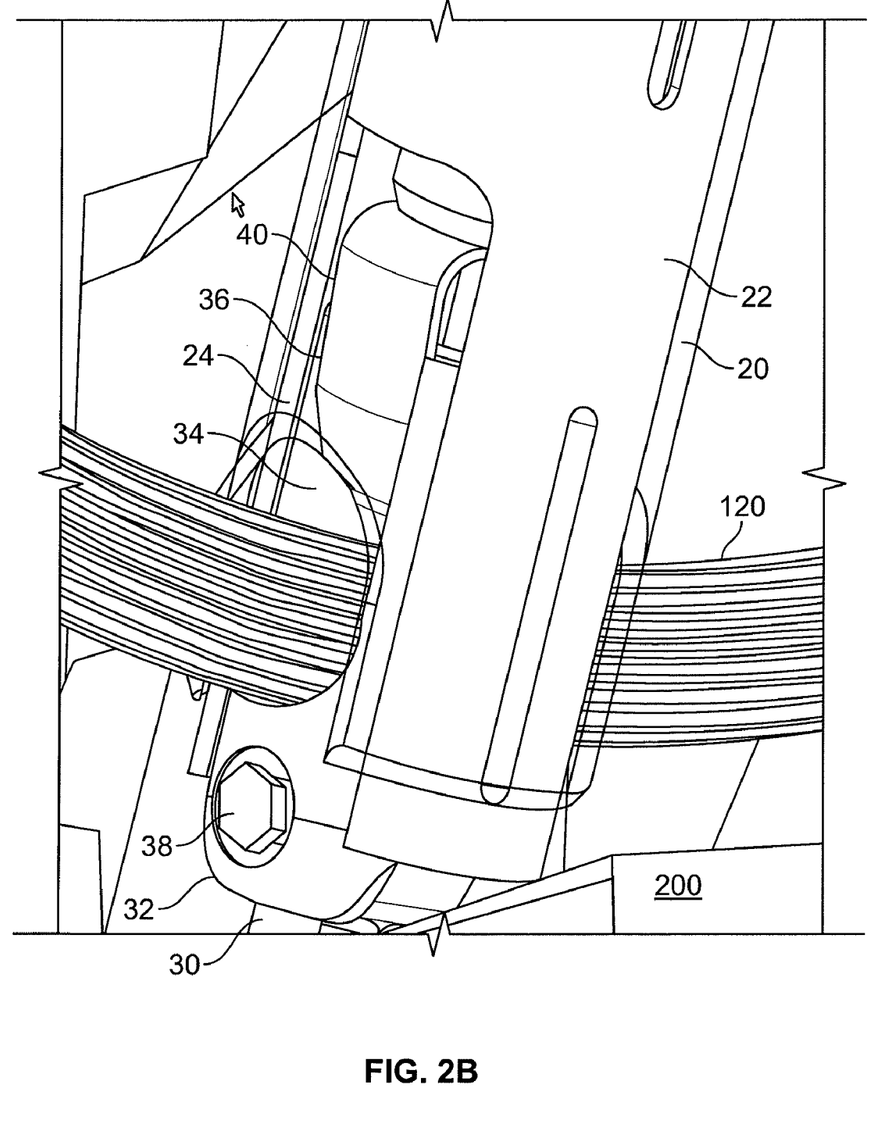
FIG. 2B is a diagram of a connecting element and bony structure interface system for engaging the connecting element to a bony structure according to various embodiments.

FIG. 2B is a diagram of a connecting element 120 and bony structure coupling system 200 for engaging the connecting element to a bony structure according to various embodiments. The bony structure coupling system 200 may include a bone screw 30 coupled to a connecting element 120 receiver 32 via a pin 38, a connecting element engaging saddle 34 rotatably coupled to a receiver locking element 36, a locking element driver 40, and a cannula couplable to the receiver 32. The locking element driver 40 may be releasably coupled to the receiver locking element 36. The cannula 22 may include a cannula slot 24 that the hook slide catch 125 of the hook slide 105 may releasably engage.

Figure 2C:
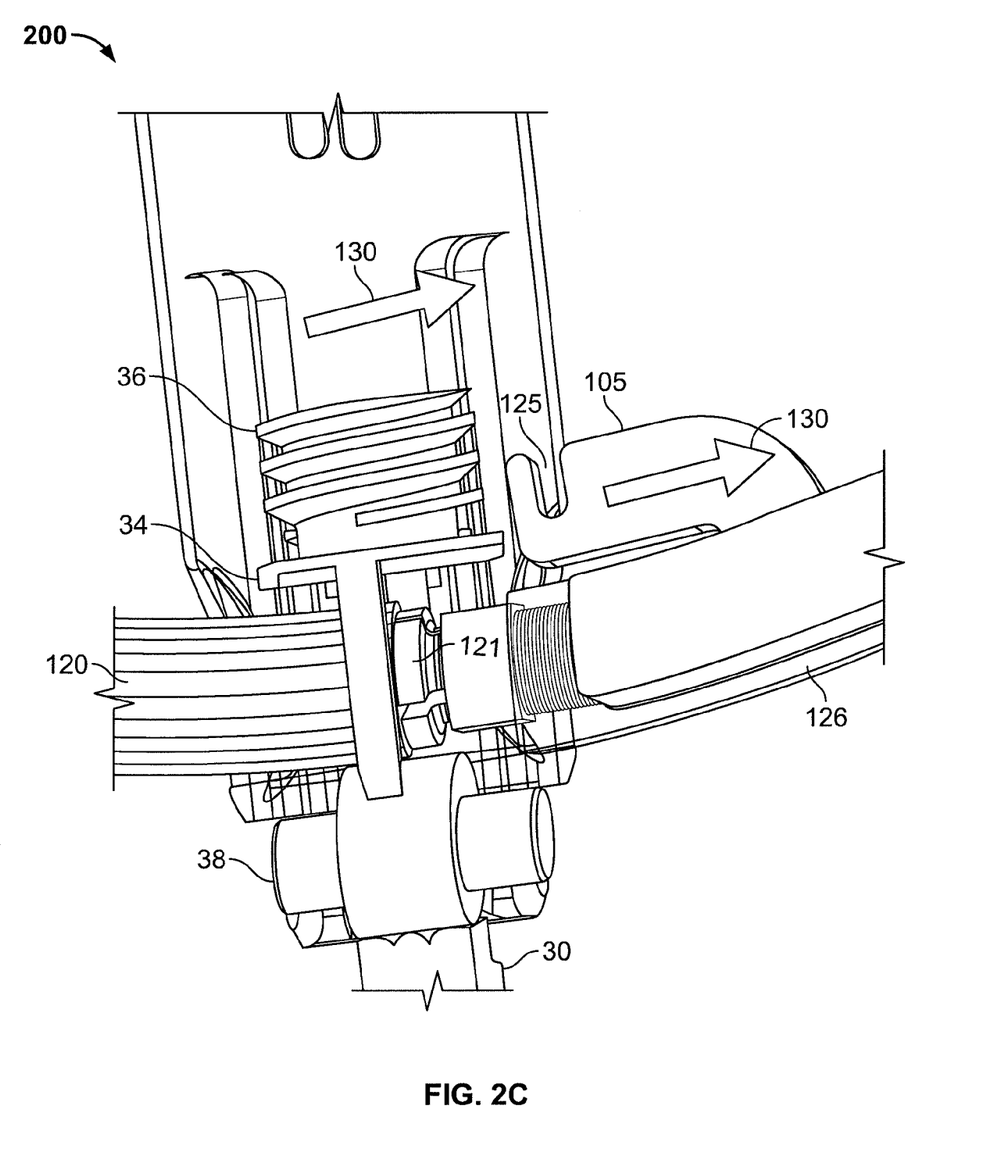
FIG. 2C is a diagram of a compressor and distracter apparatus coupled to a connecting element and a bony structure interface system to distract the bony structure relative to another structure according to various embodiments.
Figure 2D:
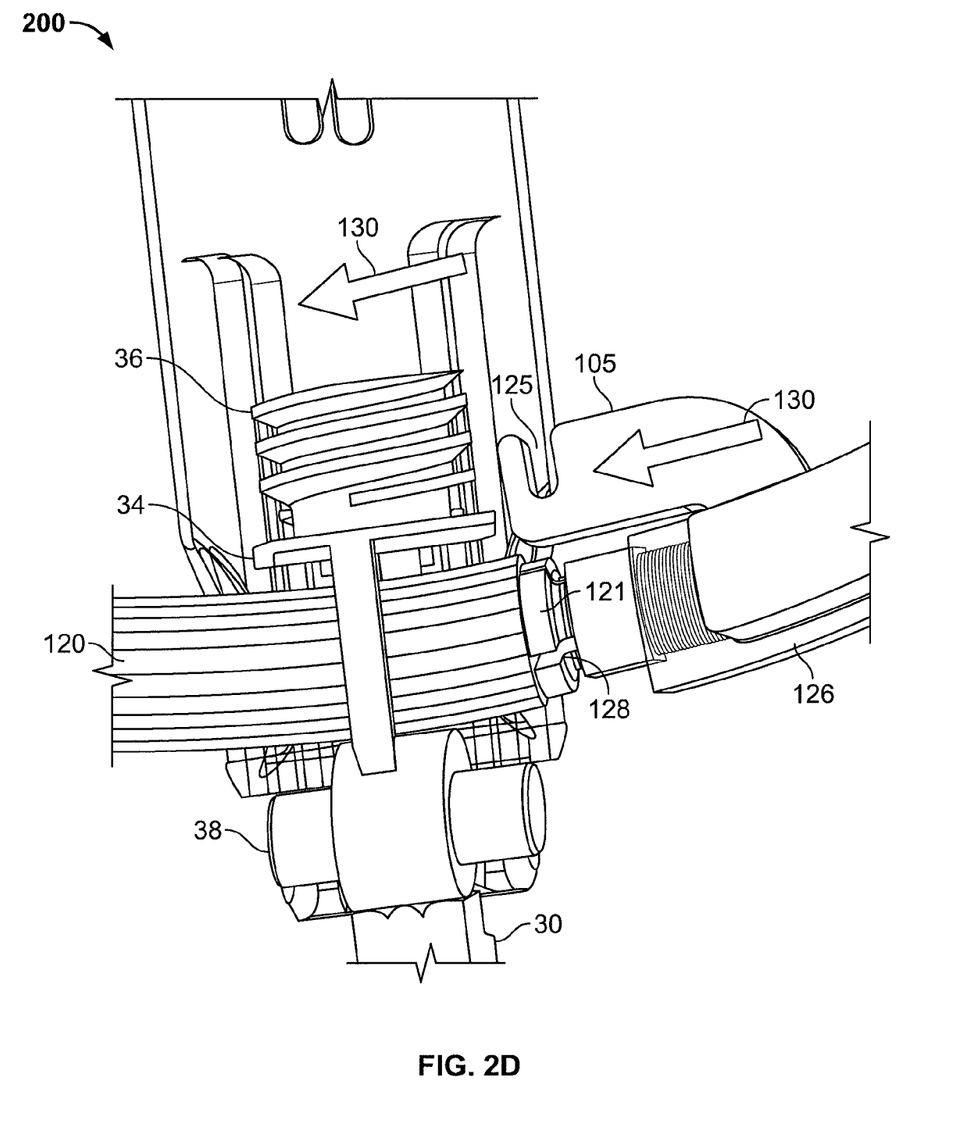
FIG. 2D is a diagram of a compressor and distracter apparatus coupled to a connecting element and a bony structure interface system to compress the bony structure relative to another structure according to various embodiments.

FIG. 2C is a diagram of the compressor and distracter apparatus 100 coupled to a connecting element 120 and a bony structure coupling system 200 to distract a bony structure coupled to the system 200 relative to another bony structure fixably coupled to the connecting element 120 according to various embodiments. As shown in FIG. 2C as the hook slide is incrementally slide away from the connecting element 120 (force vector 130), the system 200 is also distracted away from the connecting element 120. FIG. 2D is a diagram of the compressor and distracter apparatus 100 coupled to a connecting element 120 and a bony structure coupling system 200 to compress a bony structure coupled to the system 200 toward another bony structure fixably coupled to the connecting element 120 according to various embodiments. As shown in FIG. 2D as the hook slide is incrementally slide toward the connecting element 120 (force vectors 130), the system 200 is also compressed toward the connecting element 120.

Figure 2E:
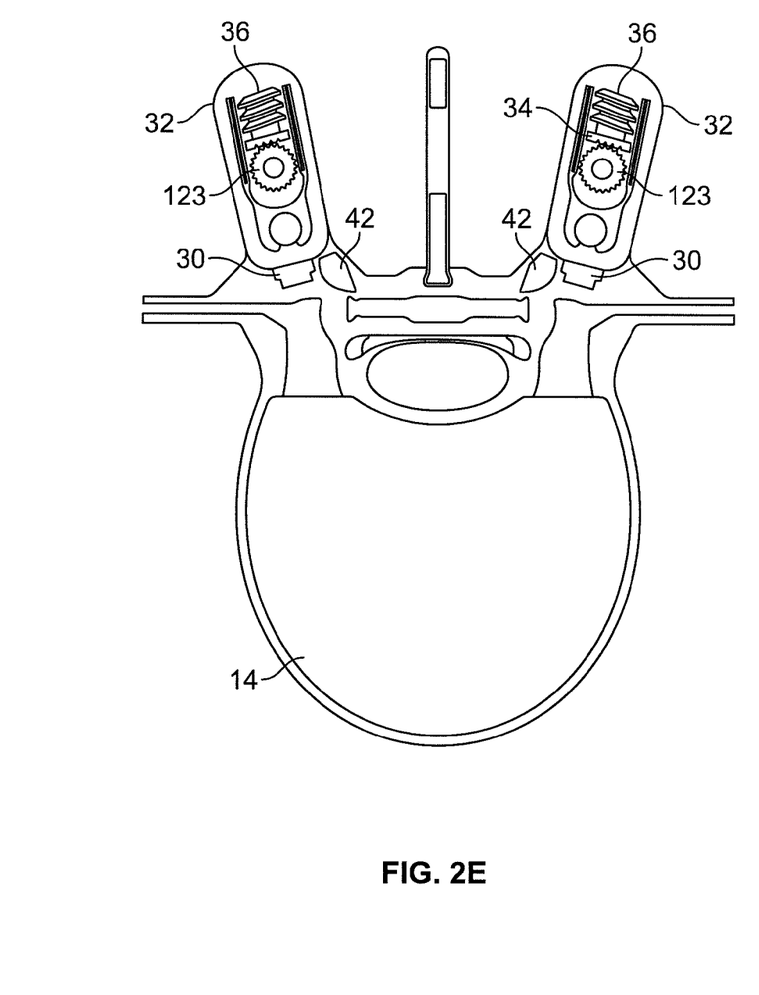
FIG. 2E is a horizontal view of two connecting elements coupled to respective bony structure interface systems, the systems coupled to a bony structure according to various embodiments.
Figure 2F:
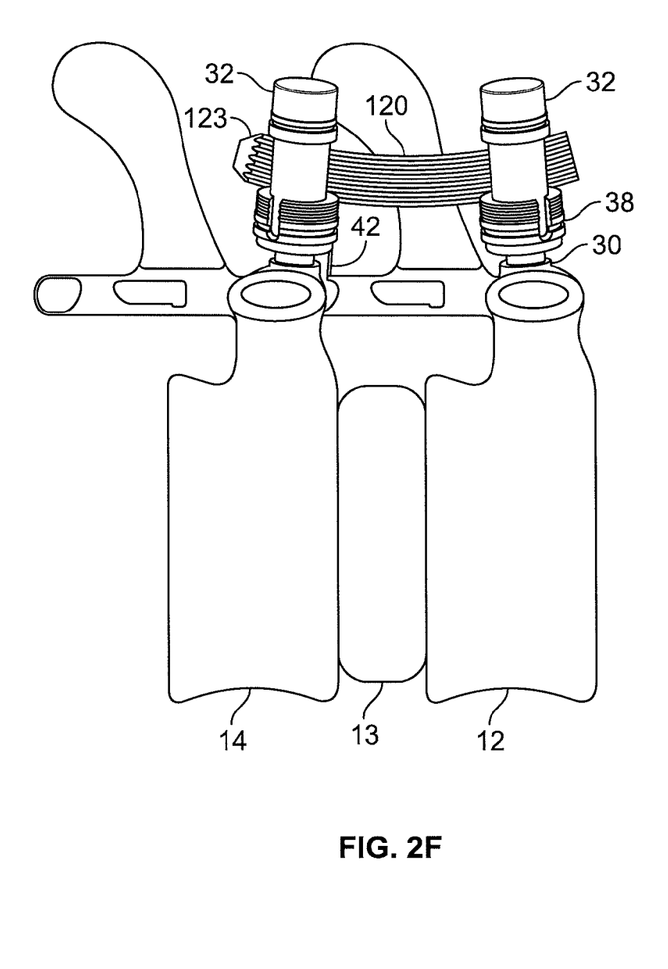
FIG. 2F is a sagittal view of a connecting element coupled to a first and a second bony structure interface system, the first system coupled to a first bony structure and the second system coupled to the second bony structure according to various embodiments.

FIG. 2E is a horizontal view of two connecting elements coupled to respective bony structure system 200, the systems coupled to a bony structure 14 according to various embodiments. In FIG. 2E a bone screw 30 in placed on a left and a right pedicle of a vertebra 14. Bone dowels 42 may also be placed in a facet joints. FIG. 2F is a sagittal view of a connecting element 120 coupled to a first and a second bony structure coupling system 200. The first system 200 may be coupled to a first bony structure 14 and the second system 200 may be coupled to the second bony structure 12 according to various embodiments. The compressor and distracter apparatus 100 may be used to distract or compress the disc space 13.

While this invention has been described in terms of a best mode for achieving the objectives of the invention, it will be appreciated by those skilled in the art that variations may be accomplished in view of these teachings without deviating from the spirit or scope of the present invention.

What is claimed is:

1. A method, including:
providing a compressor-distractor tool having (a) a handle, (b) an elongated arm extending from the handle and configured to attach to a connecting element, (c) a rigid connector slidably attached to the arm and configured to couple to a bony structure coupling system, and (d) a mechanism configured to slidably move the connector along the arm;
engaging a first bony structure coupling system that includes a first bone screw to a first bony structure;
engaging a second bony structure coupling system that includes a second bone screw to a second bony structure, wherein the second bony structure coupling system is positioned a distance from the first bony structure coupling system;
releasably engaging the first bony structure coupling system to a the slidable connector;
releasably engaging a bony structure connecting element to a distal end of the arm; and
actuating the mechanism to translate incrementally the slidable connector relative to the bony structure connection element coupler so as slidably translate the first bony structure coupling system engaged with the slidable connector and alter the distance between the first bony structure coupling system and the second bony structure coupling system.

2. The method of claim 1, wherein the distal end of the arm includes a collet that is configured to releasably engage the bony structure connecting element and wherein releasably engaging a bony structure connecting element to a distal end of the arm comprises inserting the collet into a cavity in a proximal end of the connecting element and expanding the collet so that the collet locks onto the connecting element.

3. The method of claim 1, wherein the first bony structure coupling system distracts away from the second bony structure coupling system as the slidable connector translates the first bony structure coupling system.

4. The method of claim 3, wherein the bony structure connecting element has a predetermined curvature along a longitudinal axis and the slidable connector has similar predetermined curvature along a longitudinal axis.

5. The method of claim 4, wherein the first bony structure is a vertebra and the second bony structure is a vertebra.

6. The method of claim 1, wherein engaging a first bony structure coupling system to a first bony structure comprises:
coupling a bone screw to the first bony structure;
coupling the bone screw to a receiver; and
fixably coupling the receiver to the connecting element.

7. The method of claim 1, wherein altering the distance comprises incrementally distracting the first bony structure from a second bony structure.

8. A device for compressing or distracting bones, comprising:
a handle;
an elongated arm extending distally outward from the handle along an axis, the arm having a connector adapted to releasably attach to a connecting element that can connect at a proximal region to at least a first bone structure coupling system and at a distal region to a second bone structure coupling system;
a coupler slidably attached to the arm and translatable along the axis in both a proximal and distal direction relative to the handle, wherein the coupler is configured to releasably attach to the first bony structure coupling system;
a mechanism configured to controllably translate the coupler relative to the connector upon actuation of the actuator; and
a direction selector that controls a direction of translation of the coupler relative to the connector;
wherein the coupler, when attached to the first bony structure coupling system, effects distraction or compression of the first bony structure coupling system relative to the second bony structure coupling system upon actuation of the actuator.

9. The device of claim 8, wherein the mechanism includes a ratcheting mechanism that enables a user to incrementally translate the connector in discrete increments.

10. The device of claim 8, further comprising:
the connecting element comprised of an elongated rod having a recess positioned at a proximal end of the connecting element, wherein the connector comprises a collet positionable inside the recess and configured to releasably attach to the connecting element inside the recess.

11. The device of claim 8, further comprising:
a locking pin that may be inserted into and expand the collet outward when the collet is positioned inside the recess of the connecting element.

12. The device of claim 11, wherein the locking pin when inserted through the collet fixes the elongated coupler to the connecting element.

13. The device of claim 8, wherein the coupler comprises a hook adapted to hook onto the first bony structure coupling system.

14. The device of claim 8, wherein the coupler is translatable inside the elongated arm.

* * * * *